United States Patent [19]

Young

[11] 4,375,573

[45] Mar. 1, 1983

[54] SELECTIVE PRODUCTION AND REACTION OF P-DISUBSTITUTED AROMATICS OVER ZEOLITE ZSM-48

[75] Inventor: Lewis B. Young, Skillman, N.J.

[73] Assignee: Mobil Oil Corporation, New York, N.Y.

[21] Appl. No.: 343,131

[22] Filed: Jan. 27, 1982

Related U.S. Application Data

[63] Continuation-in-part of Ser. No. 277,516, Jun. 26, 1981, abandoned, which is a continuation of Ser. No. 63,230, Aug. 3, 1979, abandoned.

[51] Int. Cl.$^3$ ............................ C07C 2/68; C07C 5/22
[52] U.S. Cl. ..................................... 585/467; 585/475
[58] Field of Search ................................. 585/467, 475

[56] References Cited

U.S. PATENT DOCUMENTS 4,117,026  9/1978  Haag et al. .......................... 585/475

Primary Examiner—Curtis R. Davis
Attorney, Agent, or Firm—Charles A. Huggett; Michael G. Gilman; Dennis P. Santini

[57] ABSTRACT

Para-Disubstituted aromatics are produced in the presence of a catalyst comprising zeolite ZSM-48. Selective cracking of para-isomers may also be accomplished to produce mixtures rich in meta-isomers.

27 Claims, No Drawings

SELECTIVE PRODUCTION AND REACTION OF P-DISUBSTITUTED AROMATICS OVER ZEOLITE ZSM-48

CROSS REFERENCE TO RELATED APPLICATIONS

This is a continuation-in-part of application Ser. No. 277,516, filed June 26, 1981, now abandoned, which was a continuation of application Ser. No. 063,230, filed Aug. 3, 1979, now abandoned.

BACKGROUND OF THE INVENTION

1. Field of the Invention

This invention relates to a new zeolite designated ZSM-48 and to its use in catalytic hydrocarbon conversion processes, and more particularly to its use in selective production of para-disubstituted aromatics.

2. Description of the Prior Art

The disproportionation of aromatic hydrocarbons in the presence of zeolite catalysts has been described in the Oil and Gas Journal, Vol. 69, No. 48 (1971). U.S. Pat. Nos. 3,126,422; 3,413,374; 3,598,878; 3,598,879 and 3,607,961 show vapor-phase disproportionation of toluene over various catalysts.

Alkylation of aromatic hydrocarbons with an olefin in the presence of a crystalline metallic aluminosilicate having uniform pore openings of about 6 to 15 Angstrom units is described in U.S. Pat. No. 2,290,607. U.S. Pat. No. 3,251,897 describes alkylation of aromatic hydrocarbons in the presence of X- or Y-type crystalline aluminosilicate zeolites, specifically such type zeolites wherein the cation is rare earth and/or hydrogen. U.S. Pat. Nos. 3,751,504 and 3,751,506 describe vapor phase alkylation of aromatic hydrocarbons with olefins, e.g. benzene with ethylene, in the presence of a ZSM-5 type zeolite catalyst.

In these prior art processes, the xylene product has the equilibrium composition of approximately 24 percent para, 54 percent meta and 22 percent ortho.

The alkylation of toluene with methanol in the presence of a cation exchanged zeolite Y has been described in the Journal of Catalysis 16, 273–280 (1970). It was reported there that selective production of p-xylene over the approximate temperature range of 200° to 275° C. with the maximum yield of p-xylene in the mixture of xylenes, i.e. about 50 percent of the xylene product mixture, being observed at 225° C. Higher temperatures were reported to result in an increase in the yield of m-xylene and a decrease in the production of para- and ortho-xylene.

Transalkylation of toluene using a catalyst of faujasite or mordenite, a Group VIII metal, such as platinum, and an additional component of arsenic, antimony, bismuth, selenium, tellurium or compounds thereof is described in U.S. Pat. No. 3,527,824.

Of the xylene isomers, i.e. ortho, meta and para-xylene, meta-xylene is the least desired product, with ortho and para-xylene being the more desired products. p-xylene is of particular value being useful in the manufacture of terephthalic acid which is an intermediate in the manufacture of synthetic fibers, such as "Dacron". Mixtures of xylene isomers, either alone or in further admixture with ethylbenzene, generally containing a concentration of about 24 weight percent para-xylene in the equilibrium mixture, have previously been separated by expensive superfractionation and multistage refrigeration steps. Such processes have high operating costs and provide limited yield.

The ZSM-5 class of zeolite catalysts have been shown to be shape selective. This shape selectivity can be further enhanced by the use of very large crystals, impregnation with Mg and P to reduce zeolite pore openings and by coke selectivation. These modified zeolite catalysts have been very effective in such reactions as selective toluene disproportionation which yields predominantly p-xylene as the product and toluene-ethylene alkylation yielding primarily p-ethyltoluene. These modification procedures are quite complex.

SUMMARY OF THE INVENTION

In accordance with the present invention, there now has been discovered that para-disubstituted aromatics such as p-xylene, p-ethyltoluene, and p-cymene are produced by alkylation catalyzed by a crystalline zeolite designated as ZSM-48. Selective cracking of p-isomers in the presence of meta-isomers may also be accomplished producing mixtures rich in the meta form.

DESCRIPTION OF THE SPECIFIC EMBODIMENTS

Zeolite ZSM-48 may be found described in co-pending U.S. Application Ser. No. 303,276, filed Sept. 17, 1981. In that application ZSM-48 is also referred to as a porous silico-crystal. The porous silico-crystal ZSM-48 can be identified in terms of moles of anhydrous oxides per 100 moles of silica as follows: (0.05 to 5) $N_2O$: (0.1 to 10)$M_{2/n}O$: (0 to 4)$Al_2O_3$: (100)$SiO_2$ wherein M is at least one cation having a valence n, N is a mixture of a $C_2$–$C_{12}$, and more preferably of a $C_3$–$C_5$ alkylamine and a tetramethyl ammonium compound and wherein the composition is characterized by the distinctive X-ray diffraction pattern as shown in Table 1 below.

The original cations can be replaced, at least in part, by calcination and/or ion exchange with another cation. Thus, the original cations are exchanged into a hydrogen or hydrogen ion precursor form or a form in which the original cation has been replaced by a metal of Groups II through VIII of the Periodic Table. Thus, for example, it is contemplated to exchange the original cations with ammonium ions or with hydronium ions. Catalytically active forms of these would include, in particular, hydrogen, rare earth metals, aluminum, metals of Groups II and VIII of the Periodic Table and manganese.

The X-ray diffraction pattern of ZSM-48 has the significant lines shown in Table 1 and is further characterized by the fact that it exhibits a singlet line within the range of 11.8±0.2 Angstrom units. Zeolite ZSM-48 does not have more than one X-ray diffraction line at 11.8±0.2 Angstrom units. The presence of only a singlet line at the indicated spacing structurally distinguishes the ZSM-48 material from closely related materials such as ZSM-12 (U.S. Pat. No. 3,832,449) which has a doublet (two lines) at 11.8±0.2 Angstrom units and high silica ZSM-12 (U.S. Pat. No. 4,104,294) which also exhibits a doublet at 11.8±0.2 Angstrom units.

TABLE 1

| Characteristics Lines of Zeolite ZSM-48 | |
|---|---|
| d(A) | Relative Intensity ($I/I_o$) |
| 11.8 ± 0.2 | S |
| 10.2 ± 0.2 | W-M |
| 7.2 ± 0.15 | W |
| 4.2 ± 0.08 | VS |

TABLE 1-continued

| Characteristics Lines of Zeolite ZSM-48 | |
|---|---|
| d(A) | Relative Intensity (I/I$_o$) |
| 3.9 ± 0.08 | VS |
| 3.6 ± 0.06 | W |
| 3.1 ± 0.05 | W |
| 2.85 ± 0.05 | W |

These values were determined by standard techniques. The radiation was the K-alpha doublet of copper, and a diffractometer equipped with a scintillation counter and a strip chart pen recorder was used. The peak heights, I, and the positions as a function of two times theta, where theta is the Bragg angle, were read from the spectrometer chart. From these, the relative intensities, 100 I/I$_o$, where I$_o$ is the intensity of the strongest line or peak, and d (obs.), the interplanar spacing in Angstroms (A) corresponding to the recorded lines, were calculated. In Table 1 the relative intensities are given in terms of the symbols W=weak, VS=very strong and W-M=weak-to-medium (depending on the cationic form). Ion exchange of the sodium ion with cations reveals substantially the same pattern with some minor shifts in interplanar spacing and variation in relative intensity. Other minor variations can occur depending on the silicon to aluminum ratio of the particular sample, as well as if it has been subjected to thermal treatment.

Zeolite ZSM-48 can be prepared from a reaction mixture containing a source of silica, tetramethyl ammonium compound, C$_2$-C$_{12}$ alkylamine, an alkali metal oxide, e.g. sodium, with or without a source alumina, and water, and having a composition, in terms of mole ratios of oxides, falling within the following ranges:

| REACTANTS | | BROAD | PREFERRED |
|---|---|---|---|
| Al$_2$O$_3$/SiO$_2$ | = | 0 to 0.08 | 0 to 0.02 |
| Na$_2$O/SiO$_2$ | = | 0.01 to 1.0 | 0.1 to 0.5 |
| N$_2$O/SiO$_2$ | = | 0.005 to 0.5 | 0.005 to 0.25 |
| OH$^-$/SiO$_2$ | = | 0.01 to 0.5 | 0.05 to 0.2 |
| H$_2$O/SiO$_2$ | = | 10 to 200 | 20 to 100 | wherein N is a mixture of a C$_2$-C$_{12}$ alkylamine and tetramethyl ammonium compound, and maintaining the mixture at 80°-200° C. until crystals of the new material are formed.

The molar ratio of C$_2$-C$_{12}$ alkylamine to tetramethyl ammonium compound is not narrowly critical and can range from 1:1 to 10:1. The tetramethyl ammonium compound can include the hydroxide or halide with the chloride being particularly preferred.

Preferably, crystallization of ZSM-48 is carried out under pressure in an autoclave or static bomb reactor at 80° to 200° C. Thereafter, the crystals are separated from the liquid and recovered. The composition can be prepared utilizing materials which supply the appropriate oxide. Such compositions include sodium silicate, silica hydrosol, silica gel, silicic acid, sodium hydroxide, and optionally a source of aluminum such as alumina gel and aluminum sulfate.

An overview of typical results obtained for several reactions is shown below:

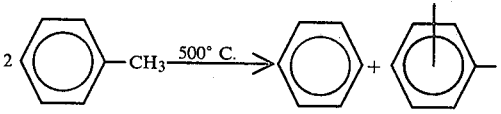

|  | Wt % In Effluent | Isomer Dist. | | |
|---|---|---|---|---|
|  |  | p | m | o |
|  | 0.5 | 33 | 51 | 16 |
|  | (Equil. | 24 | 54 | 22) |
|  | 12.6 | 50 | 30 | 20 |
|  | (Equil. | 24 | 54 | 22) |
|  | 12.5 | 47 | 52 | 1 |
|  | (Equil. | 32 | 50 | 18) |
|  | 5.2 | 67 | 28 | 5 |
|  | (Equil. | 29 | 69 | 2) |
|  | Para | 85% Conversion | | |
|  | Meta | 7% Conversion | | |

As can be seen, all reactions examined exhibited significant para selectivity.

Typical of the processes contemplated herein is the disproportionation of toluene to benzene and xylenes, wherein the proportion of para-xylene obtained is in excess of its normal equilibrium concentration. Such process is effectively carried out at a temperature of from about 350° C. to about 750° C. and a pressure of from about 1 atmosphere to about 100 atmospheres utilizing a weight hourly space velocity of toluene of from about 0.25 to about 20.

Another process involves the methylation of toluene by reaction of the latter with a methylating agent, preferably methanol, at a temperature of from about 250° C. to about 750° C. and preferably from about 325° C. to about 600° C. The reaction generally takes place at atmospheric pressure, but the pressure may be within the approximate range of 1 atmosphere to 100 atmospheres. The molar ratio of methylating agent to toluene is generally from about 0.05 to about 5. When methanol is employed as the methylating agent a suitable molar ratio of methanol to toluene has been found to be approximately 0.1 to 2 moles of methanol per mole of toluene. With the use of other methylating agents, such as methylchloride, methylbromide, dimethylether, methylcarbonate, light olefins, or dimethylsulfide, the molar ratio of methylating agent to toluene may vary within the aforenoted range. Reaction is suitably accomplished utilizing a weight hourly space velocity of from about 0.1 to about 2000 and preferably from about 1 to about 100. The reaction product consisting predominantly of para-xylene or a mixture of para- and ortho-xylene, together with comparatively smaller amounts of meta-xylene, may be separated by any suitable means, such as by passing the same through a water condenser and subsequently passing the organic phase through a column in which chromatographic separation of the xylene isomers is accomplished.

Other processes include:

(a) Toluene+ethylene→p-ethyltoluene

Reagents: preferably ethylene; also ethanol, ethylether, ethylchloride, ethylbromide, etc.
Temperature: 200°–600° C., preferably 300°–500° C.
Pressure: 0.1 atm–100 atm, preferably 1 atm–50 atm.
Molar ratio of ethylating agent to toluene of about 0.05–5, preferably 0.1–2.
Weight hourly space velocity of toluene of about 1–100.

(b) Toluene+propylene→p-cymene

Reagents: preferably propylene; also isopropylalcohol, isopropylether, isopropyl chloride, isopropyl bromide, etc.
Temperature: 150°–500° C., preferably 200°–400° C.
Pressure: 0.1–100 atm; preferably 1–50 atm.
Molar ratios: propylene, etc./toluene 0.5–5, preferably 0.1–2.
Weight hourly space velocity of toluene of about 1–100.

A still further charge stock which can be used in the process of the present invention to obtain high yields of para-xylene includes naphthenes, such as cyclopentane, cyclohexane and alkyl cyclopentanes having at least one alkyl group of 1 to 5 carbon atoms. Typical of the naphthene reactants are methyl cyclopentane, 1,2-dimethylcyclopentane and 1,3-dimethylcyclohexane. Another charge stock which can be effectively used in the present invention to selectively produce para-xylene includes paraffinic hydrocarbons having between 3 and 10 carbon atoms. Representative of such paraffins are butanes, pentanes, hexanes, heptanes, octanes and alkyl-substituted derivatives of these paraffins. Utilizing a paraffinic and/or naphthenic charge stock, reaction conditions include contact with the catalyst at a temperature of from about 400° C. to about 700° C., a pressure from about atmospheric to about 1000 psig and a weight hourly space velocity of about 0.1 to about 100.

Silico-crystal ZSM-48 may also be employed wherein an isomeric mixture of disubstituted aromatics, under conversion conditions, is contacted with ZSM-48, whereupon the 1,4-disubstituted isomer is selectively cracked or transalkylated leaving the product enriched in 1,2- and/or 1,3-disubstituted isomer. Temperature conditions are from about 150° C. to about 800° C., preferably about 250° C. to about 550° C.

The catalyst of this invention may be the product formed by impregnation of the zeolite powder or pellets with one or more alkaline earth compounds and/or ion exchanged with the same. Binders such as clays, silica, or other inorganic oxides may be used. When such as used, the total catalyst composition should preferably contain at least 50 percent by weight of crystalline ZSM-48. When the catalyst composition has the desired physical form, it is dried and then calcined at a temperature of at least about 650° C. or higher, preferably in an oxidizing atmosphere such as air.

The zeolite catalyst herein described is a member of a novel class of zeolites exhibiting some unusual properties. These catalysts induce profound transformation of aliphatic hydrocarbons to aromatic hydrocarbons in commercially desirable yields and are generally highly effective in conversion reactions involving aromatic hydrocarbons. Although they have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These catalysts retain their crystallinity for long periods in spite of the presence of steam at high temperature which induces irreversible collapse of the framework of other zeolites, e.g. of the X and A type. Further, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline zeolite, the oxygen atoms themselves being bonded to the silicon or aluminum atoms at the centers of the tetrahedra. Briefly, the preferred type catalyst useful in this invention possesses, in combination: a silica to alumina ratio of at least about 30, and preferably at least about 50 and still more preferably at least about 400; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although catalysts with a silica to alumina ratio of at least 30 are useful, it is preferred to use catalysts having higher ratios of at least about 50. Such catalysts, after activation, acquire an intracrystalline sorption capacity for normal hexane which is greater than that for water, i.e. they exhibit "hydrophobic" properties.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these catalysts ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a catalyst possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000° F. for at least 15 minutes. The catalyst is then flushed with helium and the temperature adjusted between 288° C. and 510° C. to give an overall conversion between 10% and 60%. The mixture of hydrocarbons is passed at 1 liquid hourly space velocity (i.e. 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} (\text{fraction of n-hexane remaining})}{\log_{10} (\text{fraction of 3-methylpentane remaining})}$$

The constraint index approximates the ratio of the cracking rate constants for the two hydrocarbons. Constraint Index (CI) values for some typical catalysts are:

| CAS | C.I. |
| --- | --- |
| ZSM-5 | 8.3 |
| ZSM-11 | 8.7 |
| ZSM-12 | 2 |
| ZSM-38 | 2 |
| ZSM-35 | 4.5 |
| ZSM-48 | 3.4 |
| TMA Offretite | 3.7 |

-continued

| CAS | C.I. |
| --- | --- |
| Beta | 0.6 |
| ZSM-4 | 0.5 |
| H—Zeolon | 0.5 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 288° C. to 510° C., with accompanying conversion between 10% and 60%, the constraint index may vary within the indicated approximate range of 1 to 12. Likewise, other variables such as the crystal size of the zeolite, the presence of possibly occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 288° C. to 510° C., the constraint index will have a value for any given zeolite of interest herein within the approximate range of 1 to 12.

More generally, it is desirable to activate this type catalyst by base exchange with ammonium salts followed by calcination in air at about 538° C., for example, for from about 15 minutes to about 24 hours.

The conversion processes described herein may be carried out as a batch type, semi-continuous or continuous operation utilizing a fixed or moving bed catalyst system. The catalyst after use may be conducted to a regeneration zone wherein coke is burned from the catalyst in an oxygen-containing atmosphere, e.g. air, at an elevated temperature, after which the regenerated catalyst is recycled to the conversion zone for further contact with the charge stock.

The following examples will serve to illustrate the process of the invention without limiting the same:

EXAMPLES 1 AND 2

Preparation of Catalyst ZSM-48

In these examples, the starting gel reaction mixture was prepared from sodium silicate (27.8% SiO$_2$, 8.4% Na$_2$O, 64% H$_2$O), C$_7$ (Example 1) and C$_8$ (Example 2) diamine compounds, sodium hydroxide and water. Crystallization was carried out in a stainless steel autoclave (160° C.). After crystallization, the solids were separated from any unreacted components by filtration and then water washed followed by drying at about 100° C. Preparation of these samples is further described in co-pending U.S. application Ser. No. 303,276.

The product of Example 1 had a SiO$_2$/Al$_2$O$_3$ ratio of 1340 and a crystal size of about 1.0 micron, while for the product of Example 2, SiO$_2$/Al$_2$O$_3$ was 400 and crystal size was about 0.25 micron.

As synthesized materials were worked up by calcining in helium atmosphere at 500° C. for 4 hours, ammonium exchanging twice in 2N NH₄NO₃, and calcining in air at 500° C. before use.

Catalyst testing was done on 4.0 grams of catalyst at atmospheric pressure in quartz microreactors.

EXAMPLES 3–9

The following reactions were conducted using the catalysts produced by the methods of Examples 1 and 2 which serve as further examples of the invention.

Example 3—Selective Toluene Disproportionation
Example 4—Alkylation of Toluene with Methanol
Example 5—Alkylation of Toluene with Ethylene
Example 6—Alkylation of Toluene with Ethylene
Example 7—Alkylation of Toluene with Propylene
Example 8—Alkylation of Toluene with Propylene
Example 9—Selective Cracking of Cymenes Results obtained from the exercise of the foregoing examples are listed below in Tables 2-8, respectively.

TABLE 2
TOLUENE DISPROPORTIONATION
Catalyst: Product of Example 2 (ZSM-48) $SiO_2/Al_2O_3 = 400$
Feed: Toluene

| Run | 1 | 2 | 3 |
|---|---|---|---|
| Temp. °C. | 400 | 500 | 550 |
| WHSV | 5.8 | 5.8 | 5.8 |
| Pressure, atm. | 1 | 1 | 1 |
| Product, % | | | |
| Lt Gas | .005 | .020 | .029 |
| Benzene | .052 | .384 | 1.016 |
| Toluene | 99.844 | 99.080 | 97.699 |
| para-Xylene | .035 | .157 | .369 |
| meta-Xylene | .026 | .245 | .643 |
| ortho-Xylene | .010 | .081 | .230 |
| $C_9^+$ | .029 | .033 | .014 |
| Ratio of Xylenes | | | |
| para | 49 | 32.5 | 29.7 |
| meta | 37 | 50.7 | 51.8 |
| ortho | 14 | 16.8 | 18.5 |

TABLE 3
ALKYLATION OF TOLUENE WITH METHANOL
Catalyst: Product Of Exmaple 1 (ZSM-48) $SiO_2/Al_2O_3 = 1340$
Feed: Toluene/Methanol = 4(molar ratio)

| Run | 1 | 2 | 3 | 4[a] | 5 |
|---|---|---|---|---|---|
| Temp. °C. | 350 | 400 | 450 | 450 | 400 |
| WHSV | 5.8 | 5.8 | 5.8 | 18.6 | 6.2 |
| Product, % | | | | | |
| Lt Gas | 0.73 | 0.58 | 0.43 | 0.65 | 0.47 |
| Toluene | 95.44 | 89.72 | 85.07 | 94.96 | 88.24 |
| Ethylbenzene | 0.03 | 0.03 | 0.03 | 0.03 | 0.03 |
| para-Xylene | 1.87 | 4.38 | 6.33 | 2.20 | 5.20 |
| meta-Xylene | 0.93 | 2.44 | 3.71 | 1.09 | 2.81 |
| ortho-Xylene | 0.73 | 1.80 | 2.52 | 0.80 | 1.94 |
| $C_9^+$ | 0.26 | 1.06 | 1.90 | 0.27 | 1.31 |
| Ratio of Xylenes | | | | | |
| para | 53.0 | 50.8 | 50.4 | 53.8 | 52.3 |
| meta | 26.4 | 28.3 | 29.5 | 26.6 | 28.2 |
| ortho | 20.7 | 20.9 | 20.1 | 19.6 | 19.5 |

[a]Methanol runs to 500° C. + 3.5hr calcination at 550° C. prior to this run.

TABLE 4
ALKYLATION OF TOLUENE WITH ETHYLENE
Catalyst: Product of Example 1 (ZSM-48) $SiO_2/Al_2O_3 = 1340$
Feed: Toluene/Ethylene = 5.3 (molar ratio)

| Run | 1 | 2 | 3 |
|---|---|---|---|
| Temp. °C. | 350 | 450 | 550 |
| Toluene WHSV | 6.0 | 6.0 | 6.0 |
| Product, % | | | |
| Lt Gas | 0.32 | 0.29 | 0.27 |
| Benzene | 0.02 | 0.03 | 0.11 |
| Toluene | 98.55 | 98.43 | 98.72 |
| Ethylbenzene | — | 0.01 | 0.01 |
| para-Xylene | 0.05 | 0.03 | 0.06 |
| meta-Xylene | 0.02 | 0.02 | 0.05 |
| ortho-Xylene | 0.01 | 0.01 | 0.01 |
| para-Ethyltoluene | 0.70 | 0.80 | 0.38 |
| meta-Ethyltoluene | 0.16 | 0.37 | 0.38 |
| ortho-Ethyltoluene | — | — | 0.01 |
| n-Propyltoluene | 0.17 | 0.02 | — |
| p/m/o-Ethyltoluene | 81/19/0 | 68/32/0 | 50/49/1 |
| Toluene Conv., % | 1.1 | 1.3 | 1.0 |

TABLE 5
ALKYLATION OF TOLUENE WITH ETHYLENE
Catalyst: Product of Example 2 (ZSM-48) $SiO_2/Al_2O_3 = 400$
Feed: Toluene/Ethylene = 5.2 (molar ratio)

| Run | 1 | 2 | 3 |
|---|---|---|---|
| Temp °C. | 350 | 450 | 400 |
| WHSV Toluene | 6.0 | 6.0 | 6.0 |
| Product, % | | | |
| Lt Gas | 0.41 | 0.39 | 0.41 |
| Benzene | 0.04 | 0.16 | 0.06 |
| Toluene | 86.37 | 84.93 | 84.04 |
| Ethylbenzene | 0.08 | 0.10 | 0.06 |
| para-Xylene | 0.07 | 0.09 | 0.05 |
| meta-Xylene | 0.04 | 0.12 | 0.04 |
| ortho-Xylene | 0.02 | 0.04 | — |
| para-Ethyltoluene | 5.85 | 4.64 | 6.04 |
| meta-Ethyltoluene | 6.43 | 8.49 | 8.80 |
| ortho-Ethyltoluene | 0.19 | 0.94 | 0.43 |
| n-Propyltoluene | 0.47 | 0.12 | 0.06 |
| p/m/o-Ethyltoluene | 46.9/51.6/1.5 | 33.0/60.3/6.7 | 39.6/57.6/2.8 |
| Toluene Conv., % | 13.3 | 14.7 | 15.6 |

TABLE 6
ALKYLATION OF TOLUENE WITH PROPYLENE
Catalyst: Product of Example 1 (ZSM-48) $SiO_2/Al_2O_3 = 1340$
Feed: Toluene/Propylene

| Run | 1 | 2 | 3 | 4 |
|---|---|---|---|---|
| Temp °C. | 240 | 300 | 350 | 345 |
| WHSV Toluene | 5.4 | 5.4 | 5.4 | 1.7 |
| Toluene/propylene, Mole Ratio | 4.8 | 4.8 | 4.8 | 5 |
| Liq. Prod., % | | | | |
| Lt Ends | 3.30 | 4.30 | 4.38 | 3.72 |
| Toluene | 95.78 | 93.90 | 93.53 | 92.81 |
| | — | 0.06 | 0.06 | 0.08 |
| Cymenes | | | | |
| ortho | 0.083 | 0.046 | — | 0.074 |
| meta | 0.162 | 0.139 | 0.115 | 0.306 |
| para | 0.672 | 1.437 | 1.502 | 2.104 |
| n-Propyltoluene | — | — | 0.424 | 0.908 |
| p/m/0-Cymenes | 73/18/9 | 89/9/3 | 93/7/— | 85/12/3 |
| Toluene Conv., % | 1.0 | 1.9 | 2.2 | 3.6 |

TABLE 7
ALKYLATION OF TOLUENE WITH PROPYLENE
Catalyst: Product of Example 2 (ZSM-48) $SiO_2/Al_2O_3 = 400$
Feed: Toluene/Propylene = 5.3 (molar ratio)

| Run | 1 | 2 |
|---|---|---|
| Temp. °C. | 300 | 350 |
| WHSV Toluene | 5.9 | 5.9 |

TABLE 7-continued

ALKYLATION OF TOLUENE WITH PROPYLENE

Catalyst: Product of Example 2 (ZSM-48)
$SiO_2/Al_2O_3 = 400$
Feed: Toluene/Propylene = 5.3 (molar ratio)

| Run | 1 | 2 |
|---|---|---|
| Product, % | | |
| Lt Ends | 3.46 | 4.18 |
| Toluene | 87.65 | 88.29 |
| EB, Xyl | .17 | .41 |
| Cymenes | | |
| ortho | .317 | .308 |
| meta | 1.436 | 1.234 |
| para | 3.475 | 1.401 |
| n-Propyltoluene, etc. | 3.50 | 4.18 |
| Ratio of Cymenes | | |
| para | 66.5 | 47.6 |
| meta | 27.5 | 41.9 |
| ortho | 6.1 | 10.5 |

TABLE 8

SELECTIVE CRACKING OF CYMENES

Catalyst: Product of Example 1 (ZSM-48)
$SiO_2/Al_2O_3 = 1340$

| Run | Feed | 1 | 2 |
|---|---|---|---|
| Temp. °C. | — | 400 | 300 |
| WHSV | — | 4.3 | 4.3 |
| Liquid Product Composition, % | | | |
| Lt Ends | — | 7.19 | 5.66 |
| Toluene | — | 20.91 | 14.42 |
| Cymenes | | | |
| ortho | 4.246 | 3.93 | 4.29 |
| meta | 68.130 | 63.71 | 66.43 |
| para | 27.541 | 4.26 | 9.21 |
| Off-Gas Composition, % | | | |
| $C_2^=$ | | 1.92 | 0.95 |
| $C_3^°$ | | 1.84 | 2.38 |
| $C_3^=$ | | 79.73 | 75.81 |
| $C_4^+$ | | 16.52 | 20.87 |

The examples show selectivity for formation or reaction (in case of cracking) of para-isomers substantially in excess of equilibrium.

What is claimed is:

1. A process for effecting disproportionation of toluene to produce benzene and xylenes in which the proportion of para-xylene isomer is in excess of its normal equilibrium concentration which comprises contacting toluene under conditions including a temperature of between about 350° C. and 750° C., a pressure of between about 1 atmosphere and 100 atmospheres, and a weight hourly space velocity of between about 0.25 and 20 with a catalyst comprising zeolite ZSM-48.

2. The process of claim 1 wherein said zeolite is characterized by a silica/alumina ratio in excess of 30.

3. A process for selective reaction of 1,4-disubstituted aromatic compounds in a mixture of disubstituted aromatic compounds to produce a product enriched in 1,2- and/or 1,3-disubstituted aromatic isomers which comprises contacting said mixture under conversion conditions including a temperature of between about 150° C. and about 800° C. with a catalyst comprising zeolite ZSM-48.

4. The process of claim 3 wherein said zeolite is characterized by a silica/alumina ratio in excess of 30.

5. The process of claim 2 wherein said silica/alumina ratio is at least about 50.

6. The process of claim 5 wherein said silica/alumina ratio is at least about 400.

7. The process of claim 4 wherein said silica/alumina ratio is at least about 50.

8. The process of claim 7 wherein said silica/alumina ratio is at least about 400.

9. A process for effecting the alkylation of mono-substituted aromatic compounds to produce a di-substituted aromatic product in which the para-isomer is in excess of normal equilibrium concentration which comprises contacting a mono-substituted aromatic compound with an alkylating agent under conditions effective for accomplishing said alkylation in the presence of a catalyst comprising zeolite ZSM-48.

10. The process of claim 9 wherein said mono-substituted aromatic compound is toluene and said alkylating agent is an ethylating agent.

11. The process of claim 10 wherein said ethylating agent is selected from the group consisting of ethylene, ethanol, ethylether, ethylchloride and ethylbromide.

12. The process of claim 11 wherein said ethylating agent is ethylene.

13. The process of claim 10 wherein said conditions include a temperature of between about 200° C. and 600° C., a pressure of between about 0.1 atmosphere and 100 atmospheres, a molar ratio of ethylating agent to toluene of between about 0.05 and 5, and a weight hourly space velocity of between about 1 and 100.

14. The process of claim 13 wherein said conditions include a temperature of between about 300° C. and 500° C., a pressure of between about 1 atmosphere and 50 atmospheres, and a molar ratio of ethylating agent to toluene of between about 0.1 and 2.

15. The process of claim 9 wherein said zeolite is characterized by a silica/alumina ratio in excess of 30.

16. The process of claim 15 wherein said silica/alumina ratio is at least about 50.

17. The process of claim 16 wherein said silica/alumina ratio is at least about 400.

18. The process of claim 9 wherein said mono-substituted aromatic compound is toluene and said alkylating agent is a methylating agent.

19. The process of claim 18 wherein said methylating agent is selected from the group consisting of methanol, methylchloride, methylbromide, dimethylether, methylcarbonate and dimethylsulfide.

20. The process of claim 19 wherein said methylating agent is methanol.

21. The process of claim 18 wherein said conditions include a temperature of between about 250° C. and 750° C., a pressure of between about 1 atmosphere and 100 atmospheres, a molar ratio of methylating agent to toluene of between about 0.05 and 5, and a weight hourly space velocity of between about 0.1 and 2000.

22. The process of claim 20 wherein said conditions include a temperature of between about 325° C. and 600° C., a pressure of between about 1 atmosphere and 100 atmospheres, a molar ratio of methanol to toluene of between about 0.1 and 2 and a weight hourly space velocity of between about 1 and 100.

23. The process of claim 9 wherein said mono-substituted aromatic compound is toluene, said alkylating agent is a propylating agent, and said di-substituted aromatic product comprises p-cymene.

24. The process of claim 23 wherein said propylating agent is selected from the group consisting of propylene, isopropylalcohol, isopropylether, isopropylchloride and isopropylbromide.

25. The process of claim 24 wherein said propylating agent is propylene.

26. The process of claim 23 wherein said conditions include a temperature of between about 150° C. and 500° C., a pressure of between about 0.1 atmosphere and 100 atmospheres, a molar ratio of propylating agent to toluene of between about 0.1 and 5, and a weight hourly space velocity of between about 1 and 100.

27. The process of claim 26 wherein said conditions include a temperature of between about 200° C. and 400° C., a pressure of between about 1 atmosphere and 50 atmospheres, and a molar ratio of propylating agent to toluene of between about 0.1 and 2.

* * * * *